United States Patent [19]
Pugliesi et al.

[11] Patent Number: 5,801,110
[45] Date of Patent: Sep. 1, 1998

[54] CERAMIC COMPOSITION FOR COATING SURGICAL AND DENTAL INSTRUMENTS

[75] Inventors: Robert B. Pugliesi, Woodbury; Salvatore Cucinella, Lindenhurst, both of N.Y.

[73] Assignee: Miltex Instrument Company, Lake Success, N.Y.

[21] Appl. No.: 833,540

[22] Filed: Apr. 7, 1997

[51] Int. Cl.$^6$ .................................................. C04B 35/56
[52] U.S. Cl. .................................. 501/87; 75/240; 75/242; 51/309
[58] Field of Search ........................ 501/87; 75/240, 75/242; 51/309

[56] References Cited

U.S. PATENT DOCUMENTS

| | | | |
|---|---|---|---|
| 2,471,016 | 5/1949 | Westmoreland-White | 501/87 |
| 3,711,171 | 1/1973 | Orkin et al. | 501/87 |
| 3,843,375 | 10/1974 | Murata | 501/87 |
| 4,063,908 | 12/1977 | Ogawa et al. | 501/87 |
| 4,366,254 | 12/1982 | Rich et al. | 501/87 |
| 4,425,141 | 1/1984 | Buljan et al. | 501/87 |
| 5,069,872 | 12/1991 | Penoza | 501/87 |

FOREIGN PATENT DOCUMENTS

| | | |
|---|---|---|
| 560212 | 9/1993 | European Pat. Off. . |
| 3936129 | 5/1990 | Germany . |
| 58-031059 | 2/1983 | Japan . |
| 60-009849 | 1/1985 | Japan . |
| 403231655 | 10/1991 | Japan . |
| 07305136 | 11/1995 | Japan . |

OTHER PUBLICATIONS

"New Types of Cutting Tools" Gane, J. Aust Inst. Met (1976), 21(1) pp. 24–31.

*Primary Examiner*—Paul Marcantoni
*Attorney, Agent, or Firm*—Levine & Mandelbaum

[57] ABSTRACT

The working surfaces of dental and surgical instruments are coated with a ceramic material formed by plasma spraying of a composition including a cemented carbide matrix and a ceramic dispersion to form a hardened surface with improved gripping ability. The cemented carbide matrix preferably contains tungsten and/or chromium carbide and/or cobalt. The ceramic dispersion preferably consists of alumina or other oxides.

2 Claims, 2 Drawing Sheets

CERAMIC COMPOSITION FOR COATING SURGICAL AND DENTAL INSTRUMENTS

BACKGROUND OF THE INVENTION

This invention relates to the art of coating the surfaces of working ends (jaws) of hand held surgical and dental instruments to enhance the gripping ability and wear resistance of the surfaces. More specifically, the invention is directed to a composition of matter and its application to the gripping surfaces of an instrument to improve their gripping ability and make them resistant to wear.

Hand held surgical and dental instruments have traditionally been manufactured in three forms, namely, 1) plain stainless steel with and without serrated surfaces; 2) with flame sprayed tungsten carbide surfaces; and 3) with mounted smooth and serrated tungsten carbide inserts.

The working ends (jaws) of steel instruments have a gripping surface subject to rapid wear. Flame sprayed tungsten carbide enhances the gripping ability of instrument surfaces but the flame sprayed tungsten material does not provide a gripping surface comparable to those of tungsten carbide inserts. Tungsten carbide inserts increase gripping ability and wear resistance but do not bond well to the metallic substrate of the instrument. These instruments can be separated from the instrument if the instrument is dropped or otherwise mishandled.

SUMMARY OF THE INVENTION

The aforementioned problems of the prior art are overcome by the instant invention which provides for an easy to apply, wear resistant, and very hard gripping surface for the working ends of surgical and dental instruments. The working ends, i.e., jaws of hand held surgical and dental instruments are enhanced for gripping ability by plasma spraying the jaws with a unique ceramic composition of material. The plasma sprayed ceramic composition of material adds a hard gripping surface (RC 70) to an otherwise ordinary instrument thereby increasing the gripping power and wear resistance of the instrument.

Examples of such instruments are those utilized to hold very fine gauge needles for suturing during surgical procedures. Unlike tungsten carbide inserts which are temporarily attached to the instruments, the ceramic composition of the invention is applied to the instruments by plasma spraying which allows the material to form an integral bond with the metallic substrate of the instrument. The material will not fall off or pop off if the instrument is dropped or mishandled. The composition of material of the invention is superior to prior art flame sprayed tungsten carbide surfaces in that the ceramic material provides a harder surface.

It is therefore an object of the invention to enhance the surface of a surgical or dental instrument with a coating which improves gripping ability.

Another object of the invention is to enhance the surface of a surgical or dental instrument with a coating that is wear resistant.

Still another object of the invention is to provide a coating for enhancing the gripping surfaces of a surgical or dental instrument which is easily applied and bonded to the instrument.

Other and further objects of the invention will be apparent from the following drawings and description of a preferred embodiment of the invention in which like reference numerals are used to indicate like parts in the various views.

DESCRIPTION OF THE PREFERRED EMBODIMENT

Ceramic material is extremely hard, as is desirable for the gripping surface of a dental or surgical instrument but it can also be very brittle. However, when dispersed in a cemented carbide matrix, and applied by a plasma technology process more fully described below, a surface can be obtained with the hardness of ceramic and without its brittleness.

Figures 1, 2:
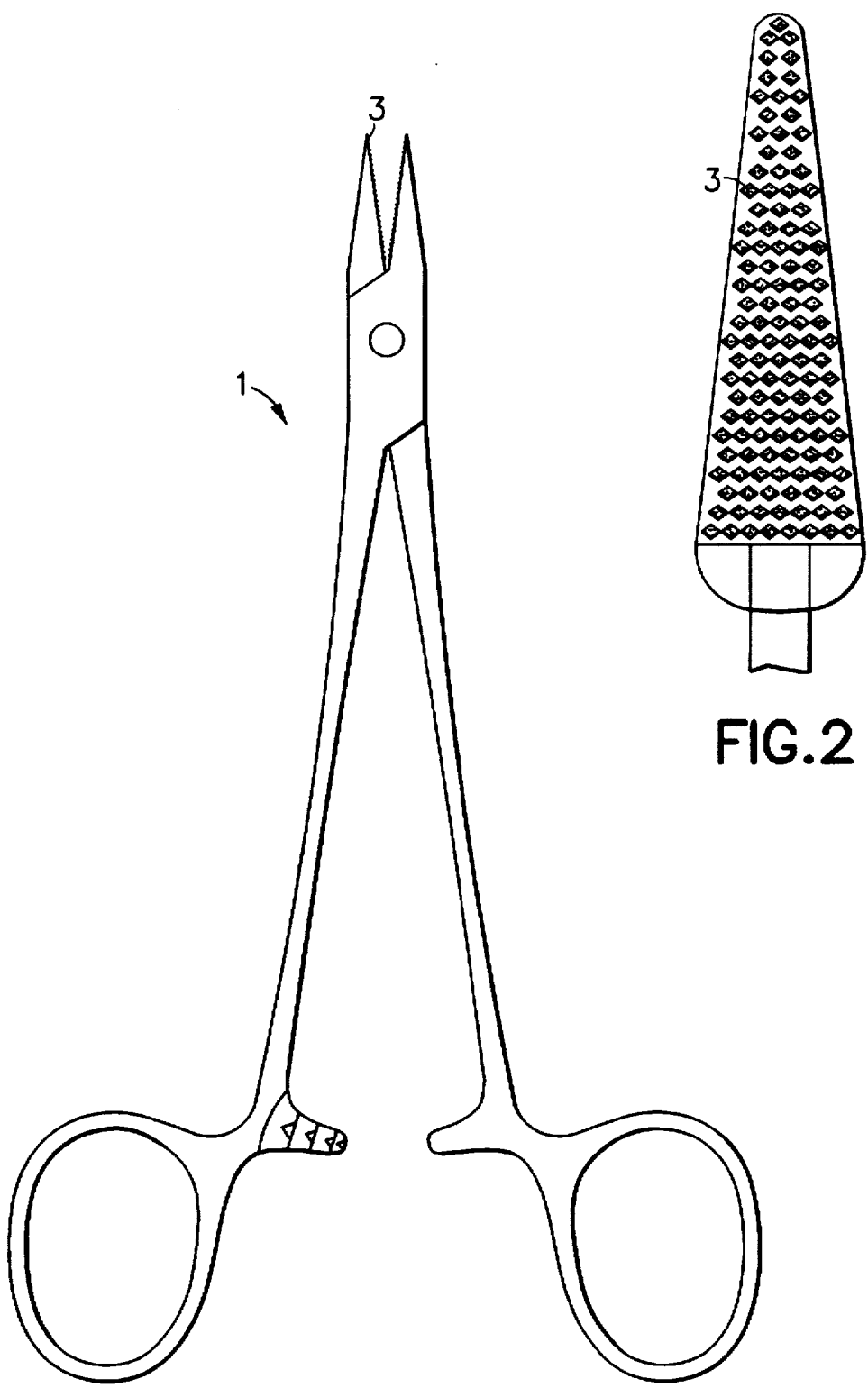
FIG. 1 is a perspective view of a ring handled needle holder with gripping surfaces coated by a composition of material in accordance with the preferred embodiment of the invention.
FIG. 2 is an enlarged fragmentary plan view of the working end of the ring handled needle holder of FIG. 1 with gripping surface coated by a composition of material in accordance with the preferred embodiment of the invention.

Referring now to FIGS. 1 and 2 of the drawings, there is shown a needle holder 1 having gripping surfaces 3 coated by a composition of material in accordance with the invention.

The composition of material in accordance with the invention consists of:

cemented carbide matrix 50%–90% ceramic material 5%–50% impurities 0%–5%

In a preferred embodiment of the invention which has been tested for gripping ability and wear resistance, the cemented carbide matrix contains a mixture of tungsten carbide and cobalt. The respective proportions of the tungsten carbide and cobalt are as follows:

tungsten carbide 75%–95% (preferably 88%) by weight cobalt 5%–25% (preferably 12%) by weight Chromium carbide may be substituted for all or part of the tungsten carbide with similar effect. Iron will often be present as an impurity in the cemented carbide matrix, typically in an amount of approximately 1%–2% of the weight of the cemented carbide matrix. Impurities consisting principally of iron can be tolerated in amounts of up to 10% by weight of the cemented carbide matrix.

The ceramic material can include oxides and organic solids. In the preferred embodiment of the invention, the ceramic material can be formed from a mixture of aluminum oxide and titanium dioxide, i.e., alumina titania. Chromium oxide can be substituted for all or part of the aluminum oxide and/or titanium dioxide.

A working ceramic material suitable for use in the invention can be consist of aluminum oxide and/or titanium dioxide and/or chromium oxide in any proportion. That is, the ceramic material may consist solely of aluminum oxide or solely of titanium dioxide or solely of chromium oxide. In a preferred embodiment of the invention, the ceramic material contains aluminum oxide in the range of 80% to 90% and titanium dioxide in the range of 10% to 20% by weight.

Hence the ceramic material to be applied to form an integral hardened surface on a dental or surgical instrument in accordance with the invention includes cobalt, carbon, iron, and/or tungsten in an amount of approximately 90% of the weight of the composition of material. The remaining 10% of the weight of the composition of material consists of a ceramic material of oxides, organic solids, alumina, and/or titanium dioxide. Combinations of the following materials can also yield acceptable results:

Cemented carbide matrix including tungsten carbide and/or chromium carbide plus, optionally, stainless steel and/or tungsten.

Ceramic material including alumina, aluminum oxide, chromium oxide, titanium dioxide, zirconium oxide, and/or nickel aluminide. Preferably, the working end of the instrument is formed from 400 series martensitic stainless steel.

The aforementioned mixture is applied to each gripping surface at the working end of a dental or surgical instrument as follows. The surfaces at the working end of an instrument on which a gripping surface is to be formed are blasted with compressed air containing aluminum oxide grit or a similar abrasive material.

The cemented carbide matrix and ceramic material are ground and and thoroughly mixed to form a homogenous powder. The homogenous powder is added to a plasma stream for spraying onto the working end of the instrument in plasma system. The plasma system preferably employs argon or nitrogen as a primary gas for forming the plasma, and hydrogen or helium as a secondary gas for adding heat and increasing the velocity of the plasma gas stream. The powder is added to the gas stream at a temperature in the range of 3300 degrees F. to 4000 degrees F., preferably 3700 degrees F. at which temperature it becomes molten.

The molten ceramic material is propelled onto the substrate whereby it becomes metallurgically bonded to it. The ceramic material exhibits a typical bond strength to the surface in excess of 5000 PSI. The thickness of the ceramic material applied to the instrument surface can be from 0.001 inches to 0.025 inches and is preferably 0.003 inches to 0.005 inches, with full thickness at the tip and tapering toward the base of the instrument.

EXAMPLE 1

A ceramic material was prepared from an alumina titanium composite material consisting of:

aluminum oxide 85.56% titanium dioxide 12.58% other oxides 1.05% organic solids 0.81%

The particle size distribution was:

U.S. Sieve +325 1.3%

U.S. Sieve −325 98.7%

The ceramic material was mixed with a cemented carbide matrix containing tungsten carbide 88% cobalt 12%

The mixture was then sprayed onto the working ends of a ring handled needle holder (see FIG. 1) made of 400 series martensitic stainless steel in a plasma deposition process. A coating having a thickness of 0.003 inches–0.005 inches measured near the tips of the instrument and tapering toward the hinge was formed.

EXAMPLE 2

The test of example 1 was repeated with chromium carbide substituted for tungsten carbide.

In each example, the instrument was then subjected to use and found to have excellent gripping ability and no measurable wear.

The ceramic coating of the invention can be used to improve the hardness and gripping ability of virtually any stainless steel surgical or dental instrument. The above described material and method for its application has been successfully used on the working end of a dental elevator, and on the opposing working ends of a spring needle holder, a tissue/suture forceps, and a dental extracting forceps. Depending on the nature of the instrument, its gripping surface or surfaces may be applied to teeth or other body tissue, or to a needle, suture or other instrument. The ceramic surface has a high coefficient of friction and good resistance to chipping, cracking, and separation from the stainless steel substrate to which it is applied.

Figure 3:
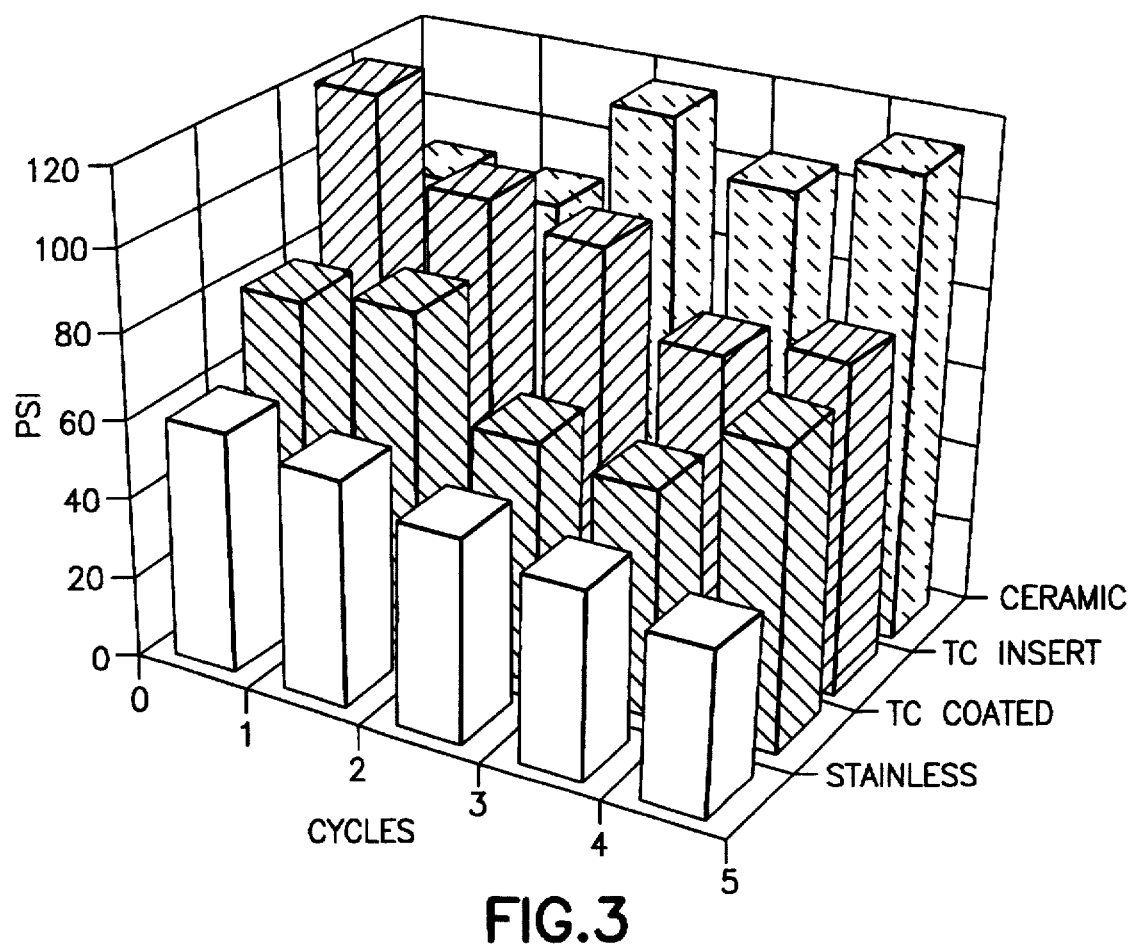
FIG. 3 is a graphical plot illustrating the gripping ability and wear resistance of a needle holder having gripping surfaces coated with the composition of material of the invention in comparison with prior art stainless steel, tungsten carbide coated, and tungsten carbide insert needle holders having gripping surfaces formed from other materials.

Referring now to FIG. 3 of the drawings, the data for the tested composition referred to above is presented. It can readily be seen that the ceramic material of the invention yielded superior gripping ability and wear resistance with respect to instrument surfaces which were uncoated stainless steel, tungsten-carbide coated, and formed on tungsten carbide inserts attached to the instrument.

It is to be appreciated that the foregoing is a description of the invention to which variations and modifications may be made without departing from the spirit and scope of the invention.

What is claimed is:

1. A composition of matter for forming a gripping surface on the working end of an instrument comprising a cemented carbide matrix selected from the group consisting of tungsten carbide and chromium carbide in an amount in the range between 50% and 90% by weight, and a ceramic material in an amount in the range between 5% and 50% by weight, of the total composition wherein the ceramic material consists of aluminum oxide in an amount of 80%–90% by weight and titanium dioxide in an amount of 10%–20% by weight.

2. A composition of matter for forming a gripping surface on the working end of an instrument comprising a cemented carbide matrix selected from the group consisting of tungsten carbide and chromium carbide in an amount in the range between 50% and 90% by weight, and a ceramic material in an amount in the range between 5% and 50% by weight, of the total composition wherein the ceramic material comprises aluminum oxide in an amount of approximately 85% by weight, and titanium dioxide in an amount of approximately 13% by weight.

* * * * *